United States Patent [19]
Hubble, III et al.

[11] Patent Number: 5,519,497
[45] Date of Patent: May 21, 1996

[54] CONTROL DEVELOP MASS IN A COLOR SYSTEM

[75] Inventors: Fred F. Hubble, III, Rochester; Michael D. Borton, Ontario; James P. Martin; Ralph A. Shoemaker, both of Rochester, all of N.Y.

[73] Assignee: Xerox Corporation, Stamford, Conn.

[21] Appl. No.: 345,037

[22] Filed: Nov. 25, 1994

[51] Int. Cl.⁶ .......................... G01N 21/47; G01N 21/55
[52] U.S. Cl. ........................................... 356/445; 356/446
[58] Field of Search ..................................... 356/445, 446

[56] References Cited

U.S. PATENT DOCUMENTS

| | | |
|---|---|---|
| 4,950,905 | 8/1990 | Butler et al. ......................... 356/446 X |
| 4,989,985 | 2/1991 | Hubble, III et al. ..................... 356/445 |
| 5,078,497 | 1/1992 | Borton et al. ............................ 356/446 |
| 5,083,161 | 1/1992 | Borton et al. ............................ 355/208 |
| 5,119,132 | 6/1992 | Butler ................................... 356/445 X |

*Primary Examiner*—Vincent P. McGraw
*Attorney, Agent, or Firm*—Ronald F. Chapuran

[57] ABSTRACT

An infrared densitometer which measures the diffuse component of reflectivity as marking particles are progressively deposited on a moving photoconductive belt. Collimated light rays are projected onto a test patch including the marking particles. The light rays reflected from the test patch are collected and directed onto a photodiode array. The photodiode array generates electrical signals proportional to the total flux and a diffuse component of the total flux of the reflected light rays. Circuitry compares the electrical signals and determines the difference to generate an electrical signal proportional to the specular component of the total flux of the reflected light rays. Additional circuitry adds the electrical signals proportional to the total flux and the diffuse component of the total flux of the reflected light rays and compares the result of the summed signal to the specular component to provide a total diffuse signal for controlling developed mass.

15 Claims, 5 Drawing Sheets

CONTROL DEVELOP MASS IN A COLOR SYSTEM

This invention relates generally to an electrophotographic printing machine, and more particularly concerns an improved infrared densitometer to detect diffuse reflectivity to control developed mass per unit area.

It is generally known in electrophotographic printing machines that toner particles are depleted from a developer mixture as toner particles are progressively deposited on a photoconductive member. As the concentration of toner particles decreases, the density of the resultant copy degrades. In order to maintain the copies being reproduced at a specified minimum density, it is necessary to regulate the concentration of toner particles in the developer mixture. This is achieved by a closed loop servo system which regulates developability.

Developability, as it pertains to an electrophotographic printing machine is the ability of the developer mixture to develop the latent image with at least a minimum specified density. It has long been recognized that a closed loop system, which regulates developability by measuring the density of the powder image developed on the photoconductive surface, optimizes cost and performance. This is due to the relative stability of the transfer and fusing processes. Also, by modulating one parameter, such as toner particle concentration, compensation for factors contributing to low copy quality, such as photoreceptor dark decay fluctuation and developer aging, can be partially accomplished.

The use of densitometers for measuring the optical density of black toner particles is well known. However, densitometers used for black toner particles are generally unsuitable for use with colored toner particles. Densitometers of this type are generally sensitive to the large component of diffusely reflected flux in the infrared from colored toner particles which gives false density measurements.

A "Toner Area Coverage Sensor" known as TACS disclosed in U.S. Pat. No. 4,989,985 was a breakthrough in the art of color densitometry. It uses flux from an infrared LED to measure the proportion of photoreceptor surface that is covered with toner. This enables one low cost device to be used to measure the developability of all colored xerographic toners measured to date, including black. In operation, flux from the top surface of an infrared LED die is directed through an aperture onto an condenser lens, where it is collimated and applied to the photoreceptor surface. The reflected flux is collected by another condenser lens and directed onto the surface of a square photodiode array having a central and 2 edge segments.

The specular component is focused to a small spot on the central segment, whereas the diffuse component floods all three segments more or less uniformly. Thus, the photo induced currents in the two edge segments are caused by the diffuse component of the total reflectivity, whereas the current in the center is caused by both the diffuse and specular. By proper choice of lens and photodiode geometry and by suitable amplification of the photo-currents, subtraction of the combined edge signals from the center signal will yield a resultant signal proportional only to the specular component for use in controlling toner mass per unit area.

A difficulty, however, with the prior art densitometer described in the '985 patent is that it is limited in range of responsivity to developed toner mass. Generally, the sensor looses sensitivity at a density greater than 0.4 milligrams per square centimeter for the toners generally used in electrophotography. It would be desirable, therefore, to provide a densitometer that provides a much greater range of sensitivity to developed toner mass, particularly at or near a maximum developed mass, which may be as high as 2.2 milligrams per square centimeter.

It is an object, therefore, of the present invention to provide a sensor capable of measuring reflectivity of toner on a photoreceptor surface to enable high toner developed mass per unit area to be controlled. It is another object of the present invention to provide a relatively simple and inexpensive sensor capable of measuring diffuse reflectivity to be able to control developed mass per unit area. Another object of the present invention is to maximize the amount of diffuse radiation used in the measurement process in order to maximize the signal to noise ratio. Other advantages of the present invention will become apparent as the following description proceeds, and the features characterizing the invention will be pointed out with particularity in the claims annexed to and forming a part of this specification.

SUMMARY OF THE INVENTION

The present invention is an infrared densitometer which measures the diffuse component of reflectivity as marking particles are progressively deposited on a moving photoconductive belt. Collimated light rays are projected onto a test patch consisting of marking particles deposited on the photoconductive belt. The light rays reflected from the test patch are collected and directed onto a photodiode array. The photodiode array generates electrical signals proportional to the total flux and a diffuse component of the total flux of the reflected light rays. Circuitry compares the electrical signals and determines the difference to generate an electrical signal proportional to the specular component of the total flux of the reflected light rays. Additional circuitry adds the electrical signals proportional to the total flux and the diffuse component of the total flux of the reflected light rays and compares the result of this summed signal to the specular component to provide a total diffuse signal for controlling developed mass.

For a better understanding of the present invention, reference may be had to the accompanying drawings wherein the same reference numerals have been applied to like parts and wherein:

BRIEF DESCRIPTION OF THE DRAWINGS

FIG. 1 schematically depicts the various components of an illustrative electrophotographic printing machine incorporating the infrared densitometer of the present invention therein. It will become evident from the following discussion that the densitometer of the present invention is equally well suited for use in a wide variety of electrostatographic printing machines, and is not necessarily limited in its application to the particular electrophotographic printing machine shown herein.

As shown in FIG. 1, a typical electrophotographic printing machine employs a photoreceptor, i.e. a photoconductive belt 10. Preferably, the photoconductive belt 10 is made from a photoconductive material coated on a grounding layer, which, in turn, is coated on an anti-curl backing layer. The photoconductive material is made from a transport layer coated on a generator layer. The transport layer transports positive charges from the generator layer. The interface layer is coated on the grounding layer. The transport layer contains small molecules of di-m-tolydiphenylbiphenyldiamine dispersed in a polycarbonate. The generation layer is made from trigonal selenium. The grounding layer is made from a titanium coated Mylar. The grounding layer is very thin and allows light to pass therethrough. Other suitable photoconductive materials, grounding layers, and anti-curl backing layers may also be employed. Belt 10 moves in the direction of arrow 12 to advance successive portions of the photoconductive surface sequentially through the various processing stations disposed about the path of movement thereof. Belt 10 is entrained about idler roller 14 and drive roller 16. Idler roller 14 is mounted rotatably so as to rotate with belt 10. Drive roller 16 is rotated by a motor coupled thereto by suitable means such as a belt drive. As roller 16 rotates, it advances belt 10 in the direction of arrow 12.

Figure 1:
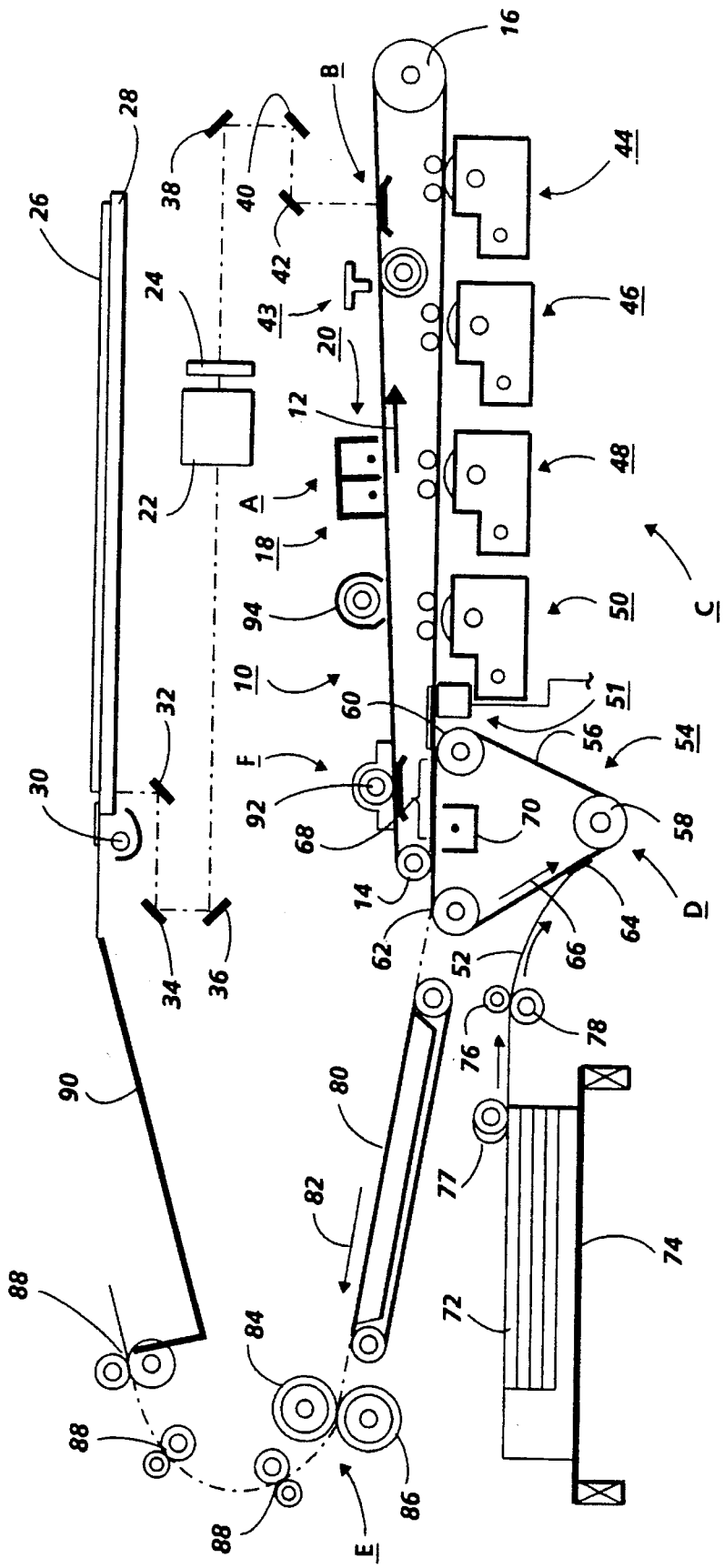
FIG. 1 is a schematic elevational view depicting an electrophotographic printing machine incorporating the infrared densitometer of the present invention.

Initially, a portion of photoconductive belt 10 passes through charging station A. At charging station A, two corona generating devices, indicated generally by the reference numerals 18 and 20 charge photoconductive belt 10 to a relatively high, substantially uniform potential. Corona generating device 18 places all of the required charge on photoconductive belt 10. Corona generating device 20 acts as a leveling device, and fills in any areas missed by corona generating device 18.

Next, the charged photoconductive surface is rotated to exposure station B. Exposure station B includes a moving lens system, generally designated by the reference numeral 22, and a color filter mechanism, shown generally by the reference numeral 24. An original document 26 is supported stationarily upon a transparent viewing platen 28. Successive incremental areas of the original document are illuminated by means of a moving lamp assembly, shown generally by the reference numeral 30. Mirrors 32, 34 and 36 reflect the light rays through lens 22. Lens 22 is adapted to scan successive areas of illumination of platen 28. The light rays from lens 22 are reflected by mirrors 38, 40, and 42 to be focused on the charged portion of photoconductive belt 10.

Lamp assembly 30, mirrors 32, 34 and 36, lens 22, and filter 24 are moved in a timed relationship with respect to the movement of photoconductive belt 10 to produce a flowing light image of the original document on photoconductive belt 10 in a non-distorted manner. During exposure, filter mechanism 24 interposes selected color filters into the optical light path of lens 22. The color filters operate on the light rays passing through the lens to record an electrostatic latent image, i.e. a latent electrostatic charge pattern, on the photoconductive belt corresponding to a specific color of the flowing light image of the original document. Exposure station B also includes a test area generator, indicated generally by the reference numeral 43, comprising a light source to project a test light image onto the charged portion of the photoconductive surface in the inter-image region, i.e. the region between successive electrostatic latent images recorded on photoconductive belt 10, to record a test area. The test area, as well as the electrostatic latent image recorded on the photoconductive surface of belt 10 are developed with toner particles at the development stations.

After the electrostatic latent image and test area have been recorded on photoconductive belt 10, belt 10 advances them to development station C. Development station C includes four individual developer units generally indicated by the reference numerals 44, 46, 48 and 50. The developer units are of a type generally referred to in the art as "magnetic brush development units." Typically, a magnetic brush development system employs a magnetizable developer material including magnetic carrier granules having toner particles adhering triboelectrically thereto.

The developer material is continually brought through a directional flux field to form a brush of developer material. The developer particles are continually moving so as to provide the brush consistently with fresh developer material. Development is achieved by bringing the brush of developer material into contact with the photoconductive surface. Developer units 44, 46, and 48, respectively, apply toner particles of a specific color which corresponds to the compliment of the specific color separated electrostatic latent image recorded on the photoconductive surface. The color of each of the toner particles is adapted to absorb light within a preselected spectral region of the electromagnetic wave spectrum corresponding to the wave length of light transmitted through the filter. For example, an electrostatic latent image formed by passing the light image through a green filter will record the red and blue portions of the spectrums as areas of relatively high charge density on photoconductive belt 10, while the green light rays will pass through the filter and cause the charge density on the photoconductive belt 10 to be reduced to a voltage level ineffective for development.

The charged areas are then made visible by having developer unit 44 apply green absorbing (magenta) toner particles onto the electrostatic latent image recorded on photoconductive belt 10. Similarly, a blue separation is developed by developer unit 46 with blue absorbing (yellow) toner particles, while the red separation is developed by developer unit 48 with red absorbing (cyan) toner particles. Developer unit 50 contains black toner particles and may be used to develop the electrostatic latent image formed from a black and white original document. Each of the developer units is moved into and out of the operative position.

In the operative position, the magnetic brush is closely adjacent the photoconductive belt, while, in the non-operative position, the magnetic brush is spaced therefrom. During development of each electrostatic latent image only one developer unit is in the operative position, the remaining developer units are in the non-operative position. This ensures that each electrostatic latent image and successive test areas are developed with toner particles of the appropriate color without co-mingling. In FIG. 1, developer unit 44 is shown in the operative position with developer units 46, 48 and 50 being in the non-operative position. The developed test area passes beneath an infrared densitometer, indicated generally by the reference numeral 51. Infrared densitometer 51 is positioned adjacent the photoconductive surface of belt 10 to generate electrical signals proportional to the developed toner mass of the test area. The detailed structure of densitometer 51 will be described with reference to FIGS. 2 through 5.

After development, the toner image is moved to transfer station D where the toner image is transferred to a sheet of support material 52, such as plain paper amongst others. At transfer station D, the sheet transport apparatus, indicated generally by the reference numeral 54, moves sheet 52 into contact with photoconductive belt 10. Sheet transport 54 has a pair of spaced belts 56 entrained about three rolls 58, 60 and 62. A gripper 64 extends between belts 56 and moves in unison therewith. Sheet 52 is advanced from a stack of sheets 72 disposed on tray 74. Feed roll 77 advances the uppermost sheet from stack 72 into the nip defined by forwarding rollers 76 and 78. Forwarding rollers 76 and 78 advance sheet 52 to sheet transport 54. Sheet 52 is advanced by forwarding rollers 76 and 78 in synchronism with the movement of gripper 64.

In this way, the leading edge of sheet 52 arrives at a preselected position to be received by the open gripper 64. The gripper then closes securing the sheet thereto for movement therewith in a recirculating path. The leading edge of the sheet is secured by gripper 64. As the belts move in the direction of arrow 66, the sheet 52 moves into contact with the photoconductive belt, in synchronism with the toner image, at the transfer zone 68. A corona generating device 70 sprays ions onto the backside of the sheet so as to charge the sheet to the proper magnitude and polarity for attracting the toner image from photoconductive belt 10. Sheet 52 remains secured to gripper 64 so as to move in a recirculating path for three cycles. In this way, three different color toner images are transferred to sheet 52 in superimposed registration with one another.

After the last transfer operation, grippers 64 open and release sheet 52. Conveyor 80 transports sheet 52, in the direction of arrow 82, to fusing station E where the transferred image is permanently fused to sheet 52. Fusing station E includes a heated fuser roll 84 and a pressure roll 86. Sheet 52 passes through the nip defined by fuser roll 84 and pressure roll 86. The toner image contacts fuser roll 84 so as to be affixed to sheet 52. Thereafter, sheet 52 is advanced by forwarding roll pairs 88 to catch tray 90 for subsequent removal by the machine operator.

The last processing station in the direction of movement of belt 10, as indicated by arrow 12 is cleaning station F. A rotatably mounted fibrous brush 92 is positioned in cleaning station F and maintained in contact with photoconductive belt 10 to remove residual toner particles remaining after the transfer operation. Thereafter, lamp 94 illuminates photoconductive belt 10 to remove any residual charge remaining thereon prior to the start of the next successive cycle.

Figure 2:
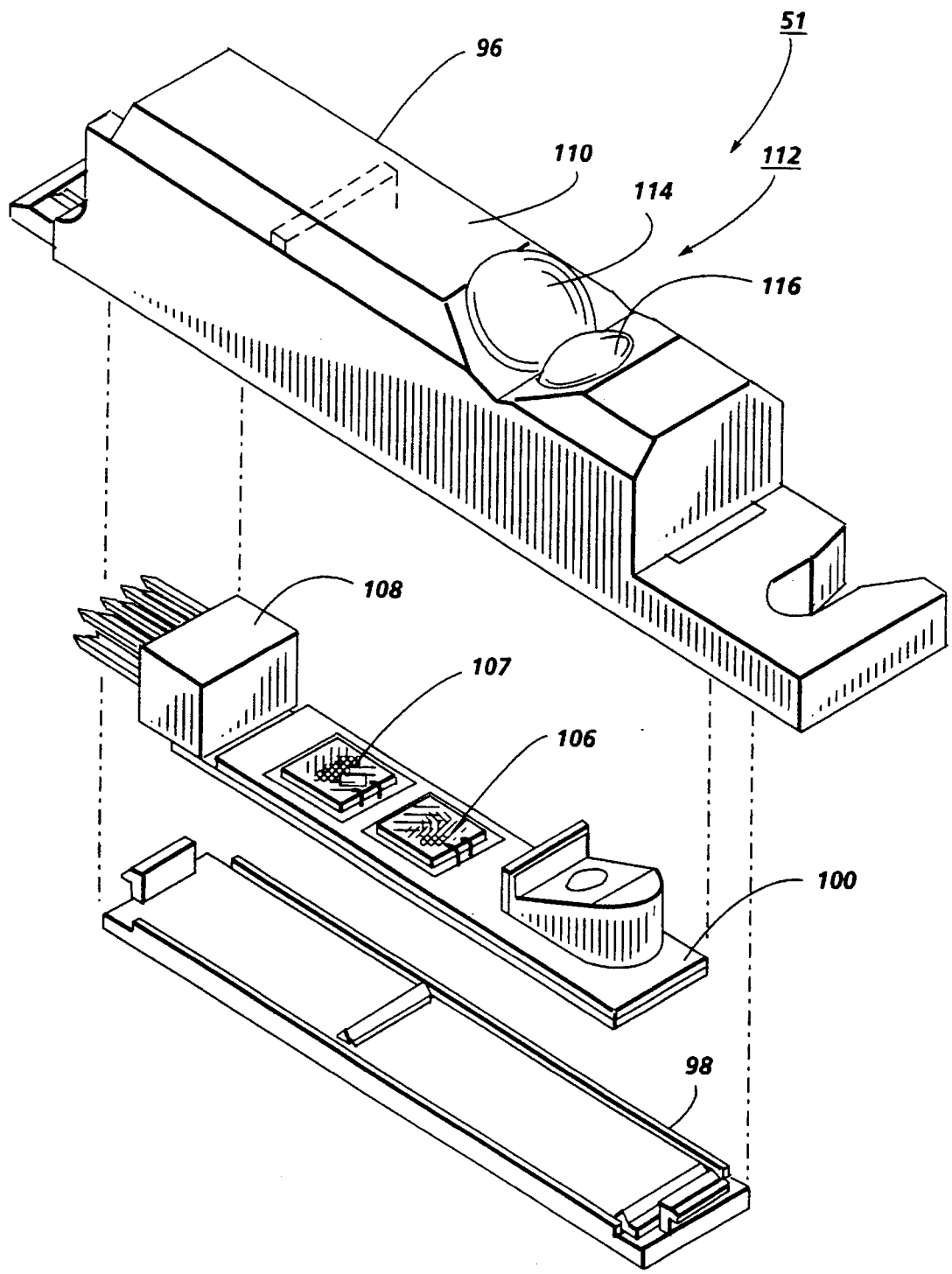
FIG. 2 is a perspective view showing the densitometer used in the FIG. 1 printing machine.
Figure 3:
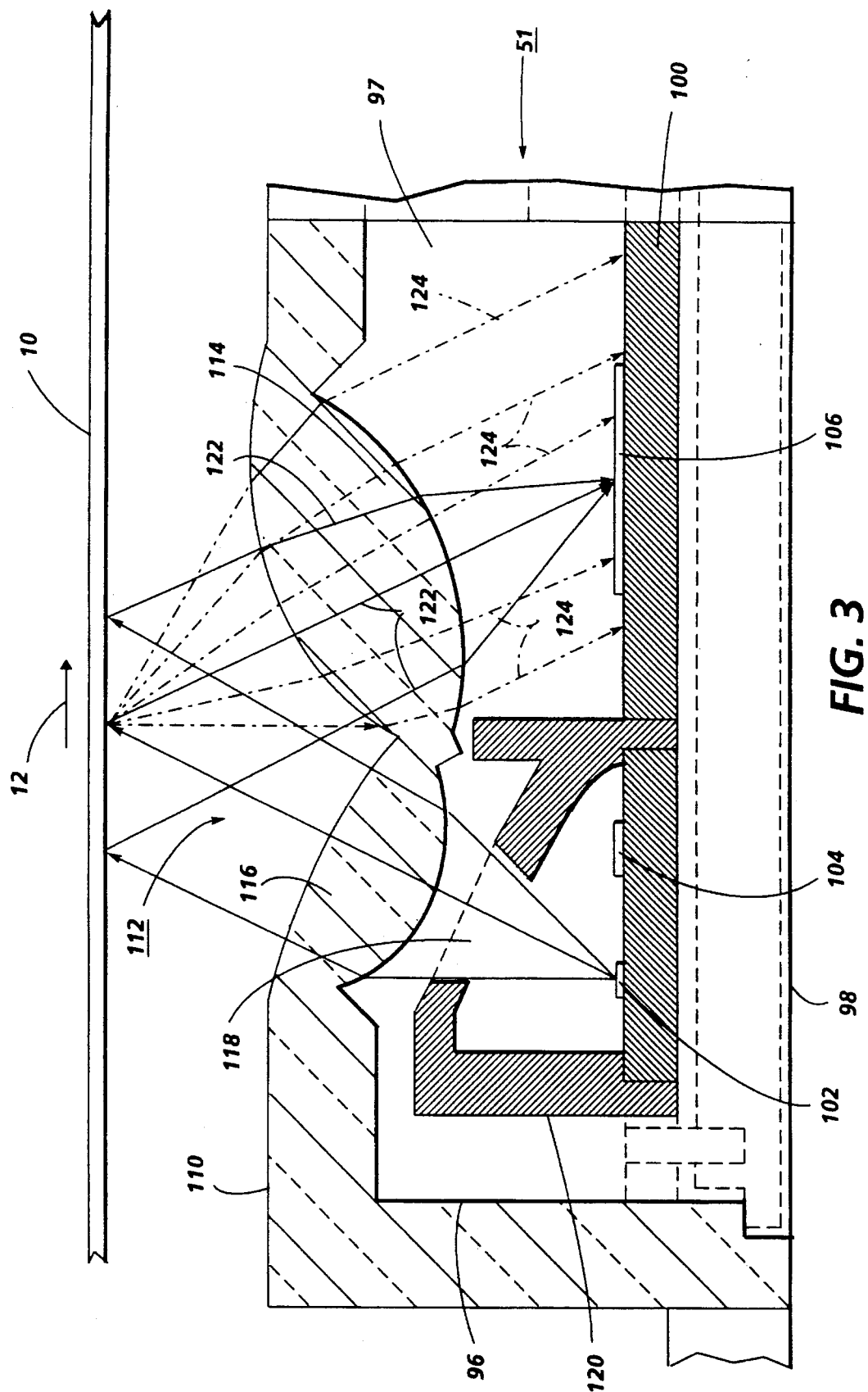
FIG. 3 is a fragmentary, sectional elevational view of the FIG. 2 densitometer.

Referring now to FIGS. 2 and 3, there is shown infrared densitometer 51 in greater detail. Densitometer 51 includes a generally rectangularly shaped molded housing 96 made preferably from an acrylic material or any other suitable optically transparent material. Housing 96 defines a chamber 97. A cover 98 encloses the bottom of housing 96. A printed circuit wiring board 100 is mounted between cover 98 and housing 96 in chamber 97. Printed circuit board 100 supports a suitable light emitting diode (LED) 102 for providing light rays to illuminate the marking particles adhering to the photoconductive surface of belt 10. A control photodiode 104 and a photodiode array 106 are also mounted on printed circuit board 100. The details of photodiode array 106 will be described with reference to FIG. 4.

Connector 108 is also mounted on printed circuit board 100. An integrated circuit chip, indicated generally by the reference numeral 107, is electrically connected to LED 102, photodiode 104 and photodiode array 106 to provide drive current to LED 102 and to process the signals from photodiode 104 and photodiode array 106. The top surface 110 of housing 96 defines a V-shaped recess, generally indicated by the reference numeral 112. One surface of the V-shaped recess 112 supports a condenser lens 116 which is an integral collimating lens. The other surface of the V-shaped recess 112 supports another condenser lens 114 which is an integral collector lens. LED 102 generates near infrared light rays which are transmitted through an aperture 118 in housing 120 onto condenser lens 116. Condenser lens 116 collimates the light rays and focuses the light rays onto the marking or toner particles deposited on the test area recorded on the photoconductive surface of belt 10.

Photodiode 104 is positioned to receive a portion of the LED radiant flux reflected from the walls of housing 120. The output signal from photodiode 104 is compared with a reference signal and the resultant error signal used to regulate the input current to LED 102 to compensate for LED aging and thermal effects. The light rays reflected from the test patch are collected by condenser lens 114 and directed onto the surface of photodiode array 106. The specular component of the reflected light rays or flux, as shown by arrows 122, is focused on a small spot on surface of the central segment of photodiode array 106. The diffuse components of the reflected light rays or flux, as shown by arrows 124, flood the entire surface of photodiode array 106. Further details of the structure of the densitometer, exclusive of photodiode array 106, may be found in U.S. Pat. No. 4,553,033 issued to Hubble, III et al. on Nov. 12, 1985, the relevant portions thereof being hereby incorporated into the present application.

Figure 4:
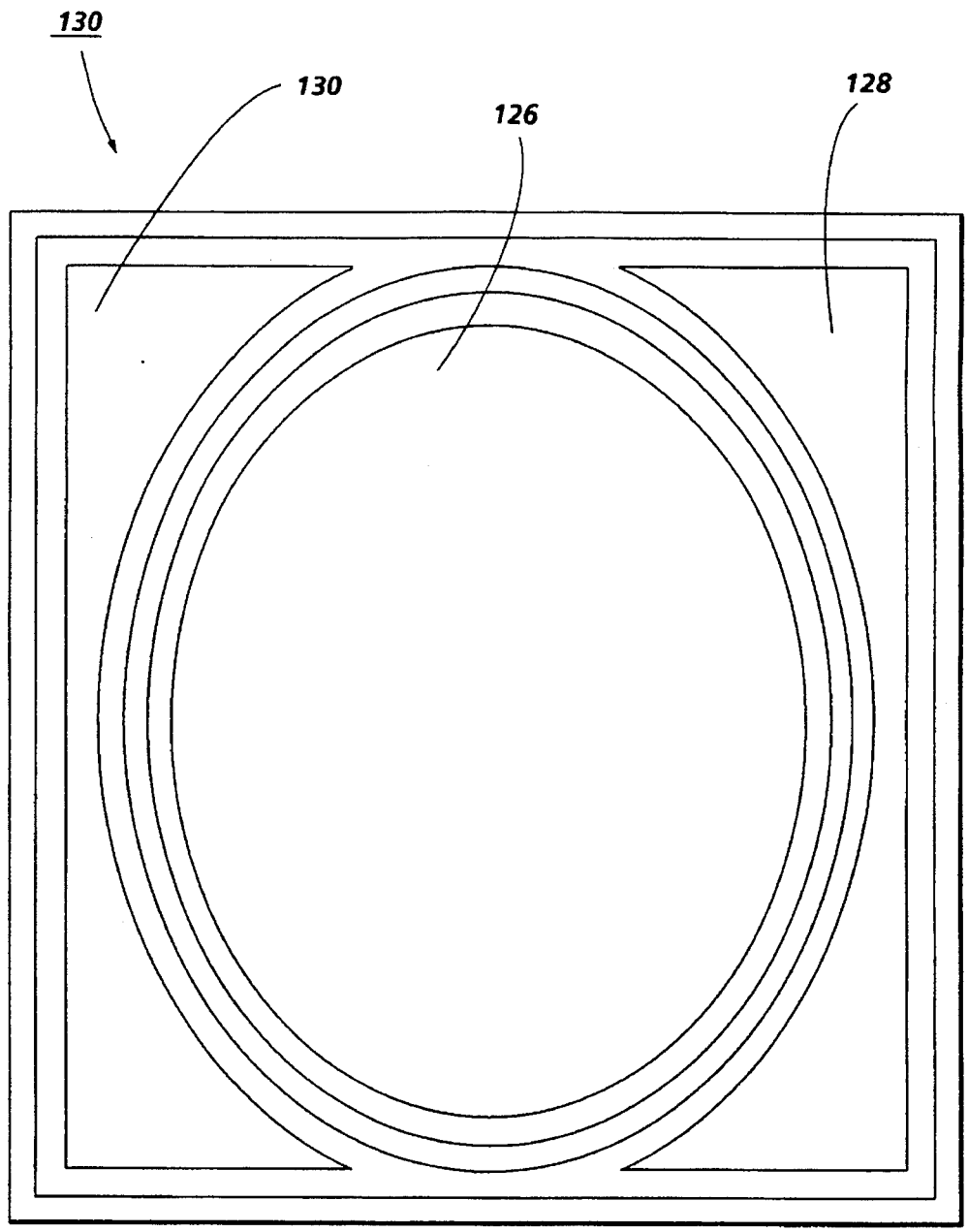
FIG. 4 is an enlarged plan view of the photodiode array used in the FIG. 3 densitometer.

Turning now to FIG. 4, there is shown photodiode array 106 in greater detail. Preferably, photodiode 106 is about 5 millimeter square. Photodiode array 106 receives the light rays transmitted through condenser lens 116. These light rays are reflected from the toner particles adhering to the photoconductive surface of belt 10 and the exposed portion of the photoconductive surface of belt 10 which lies between the toner particles. A central photodiode 126 receives the total reflected light rays or flux. The total reflected light rays or flux includes the specular component and the diffuse component of the reflected light rays or flux. Thus, central photodiode 126 generates an electrical signal proportional to the total reflected flux including the diffuse component and the specular component. As shown, central photodiode 126 is preferably substantially elliptical. Edge photodiodes 128 and 130 are configured to compliment central photodiode 126 to complete photodiode array 106 which is substantially square in shape.

Edge photodiodes 128 and 130 are substantially identical to one another, being shaped as mirror images of one another. Edge photodiodes 128 and 130 are positioned to receive only the diffuse component of the reflected light rays or flux transmitted through condenser lens 116. Hence, the electrical signal generated by edge photodiodes 128 and 130 is proportional to only the diffuse component of the reflected light rays or flux. Subtraction of the combined electrical signals of the edge photodiodes from the electrical signal from the central photodiode yields a resultant electrical signal proportional to the specular component of the light rays or flux reflected from the toner particles and the exposed portion of the photoconductive surface of belt 10. A block diagram reflecting the integrated circuit 107 used to measure the specular component of the light rays is shown in FIG. 5.

Figure 5:
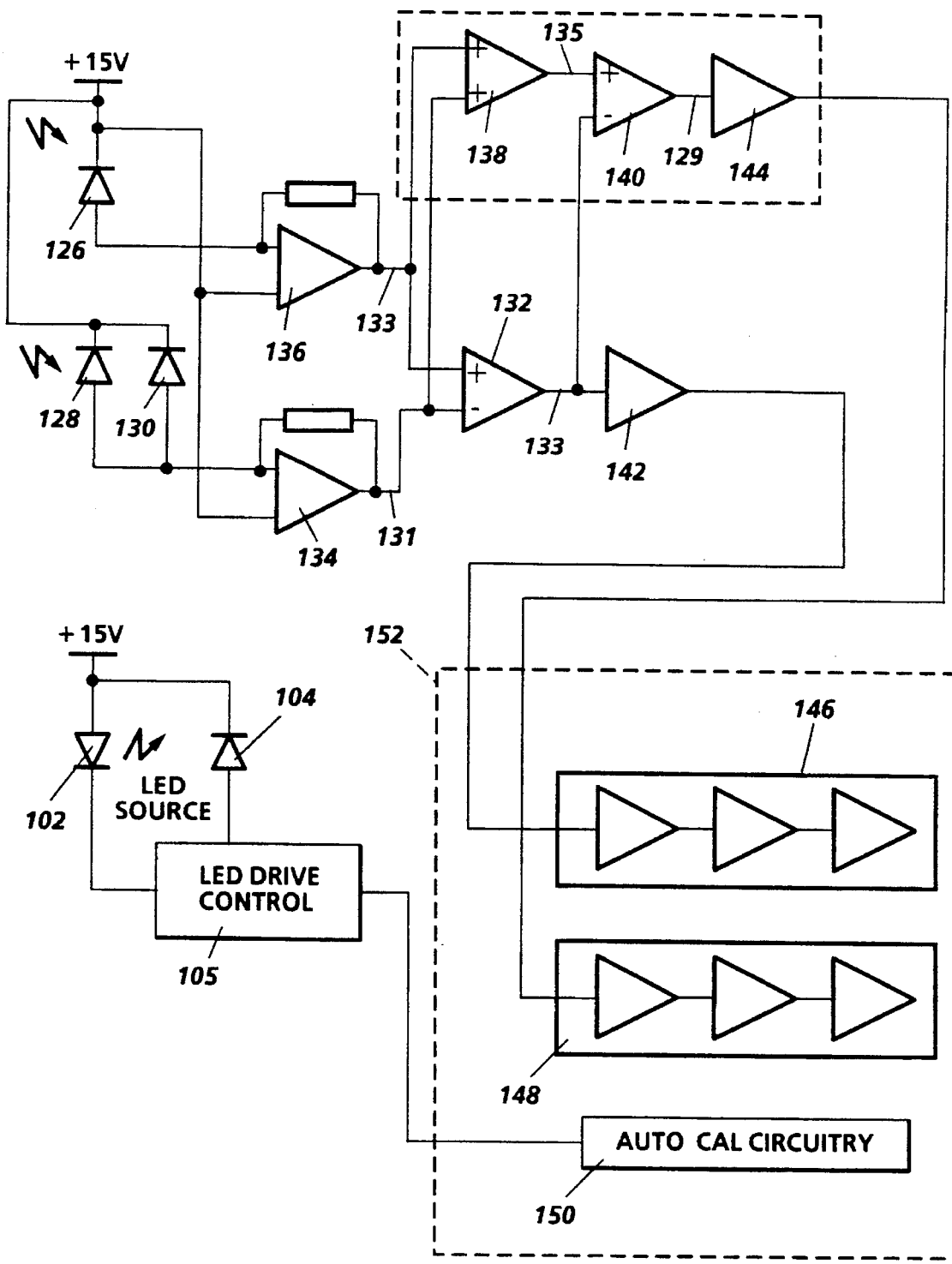
FIG. 5 is a block diagram of the control logic associated with the FIG. 3 densitometer in accordance with the present invention.

As shown in FIG. 5, central photodiode 126 generates an electrical signal proportional to the the sum of the specular and diffuse components of the light rays. Central photodiode 126 is electrically connected to amplifier 136. The electrical output signals from photodiodes 128 and 130 are proportional to the diffuse component of the light rays. Photodiodes 128 and 130 are electrically connected to amplifier 134. The electrical signals from photodiodes 128 and 130 are combined in amplifier 134 and transmitted to difference amplifier 132 along with the signal from amplifier 136 receiving an input signal from photodiode 126.

The voltage output from difference amplifier 132, illustrated as 133, is proportional only to the specular component of the current output. This voltage output provides a measure of the area coverage of colored toner particles deposited on the photoconductive surface. This may be seen more clearly from the following Table which provides the approximate reflective properties of selected photoreceptor and toner materials at 880 nanometers incident wavelength.

| SURFACE | SPECULAR REFLECTIVITY | DIFFUSE REFLECTIVITY |
| --- | --- | --- |
| Photoreceptor | 5–16% | 12–26% |
| Yellow Toner | 0% | 60% |
| Magenta Toner | 0% | 64% |
| Cyan Toner | 0% | 44% |
| Black Toner | 0% | 1% |

Thus, when 100% of the test area is developed with toner particles, the specular reflectivity is zero and the output from difference amplifier 132 will be zero. When the test area is undeveloped, i.e. 0% of the test area is developed with toner particles, the output will correspond to the specular reflectivity of the photoreceptor whose specular reflectivity is non-zero.

With continued reference to FIG. 5, the electrical signal from control photodiode 104 is transmitted through suitable circuitry to generate a voltage output which regulates LED drive control 105. The drive control energizes LED 102. In this way, a feedback loop is formed for driving LED 102 to provide a relatively constant output. Thus, if the signal from the photodiode changes, the output from drive control 105 is suitably adjusted to maintain a relatively constant light output from the LED 102.

With further reference to FIG. 5, in accordance with the present invention, a total diffuse signal, illustrated at 129, is provided rather than the partial diffuse signal, 131 that is the output of amplifier 134 interconnected to diodes 128 and 130. The total diffuse signal 129 is provided by the difference amplifier 140 receiving inputs from the summing amplifier 138 and the difference amplifier 132. In particular, the summing amplifier 138 receives two signals representative of diffuse reflection, namely diffuse signal 131 which is a measure of the diffuse reflection sensed by the edge photodiodes 128 and 130 as well as the diffuse component captured by the central photodiode 126 included as part of the signal 133 output from amplifier 136. Thus, the signal 135 output from the summing amplifier 138 is a measure of a total reflection onto photodiode array 106 including the specular and diffuse components provided by diode 126. In particular, the specular component is provided by diode 126 and diffuse components are provided by diodes 126, 128 and 130.

In order to provide a signal representing of the total diffuse reflection for controlling developed mass per unit area without a specular component, it is necessary to subtract out the specular component in the signal 135. To this end difference amplifier 140 receives both signals 135 from summing amplifier 138 as well as the specular signal 133 from difference amplifier 132. Thus the signal 129 is proportional to the diffuse flux or reflection collected by both the edge photo detectors as well as the photodetector center. By using the diffuse flux component of all three diodes, higher photo currents typically result with higher signal to noise ratios. It should be noted that prior art efforts using only the edge photo detectors for defuse flux collection showed photo currents typically in the ten to fifty nano-amp range which were thought to be too low to enable a reliable control. However, it has been discovered that the signals, if properly amplified, and shielded are sometimes usable.

FIG. 5 illustrates additional circuitry such as amplifier 144 to buffer the signal 129 which is then sent to a remote printed wiring board, illustrated at 152, for processing by sample and hold and buffering circuitry 148. In addition, the specular signal 133 is buffered at amplifier 142 for transmission to the remote printed wiring board 152 to sample and hold and buffering circuitry 146. Also, the signal from the feedback photodiode 104 is fed from the LED drive control 105 to provide a signal to the automatic calibration circuitry 150 at the remote printed wiring board 152. It should be noted that with the circuitry shown in FIG. 5, it is possible to extend the range of control of developed mass per unit area from 0.4 milligrams per square centimeter to 2.5 milligrams per square centimeter. Thus the device is capable of reliably measuring high toner developed mass per unit area, particularly required for color toner development.

While the invention has been described with reference to the structure disclosed, it is not confined to the details set forth, but it is intended to cover such modifications or changes as may come within the scope of the following claims.

We claim:

1. An infrared densitometer for measuring the diffuse component of the reflectivity of marking particles deposited on a moving photoconductive belt, including a collimating lens;

a light source positioned to project light rays through said collimating lens onto a test patch including marking particles deposited on the moving photoconductive belt;

a collector lens positioned to receive the light rays reflected from the test patch on the moving photoconductive belt;

a photosensor array positioned to receive the light rays transmitted through said collector lens and generating a total signal proportional to the total reflectivity of at least the test patch and a diffuse signal proportional to the diffuse component of the reflectivity of the test patch; and a first circuit electrically connected to said photosensor array for comparing the total signal and the diffuse signal proportional to the diffuse component for generating a specular signal proportional to the specular component of the total reflectivity of the test patch wherein the improvement comprises a second circuit electrically connected to said first circuit for comparing the sum of the total signal and the diffuse signal with the specular signal for generating a total diffuse signal proportional to the diffuse component of the total reflectivity of the test patches.

2. An apparatus according to claim 1 wherein the first circuit includes a difference amplifier responding to the total signal proportional to the total reflectivity and a diffuse signal proportional to the diffuse component to provide the specular signal.

3. An apparatus according to claim 1 wherein the second circuit includes a summing amplifier to add the total signal and the diffuse signal to provide a total diffuse and specular signal.

4. An apparatus according to claim 3 wherein the second circuit includes a difference amplifier responding to the total diffuse and specular signal and the specular signal to provide said total diffuse signal.

5. An apparatus for measuring the diffuse reflectance of marking particles deposited on a surface, including:
   a light source for projecting light rays onto a test patch including the particles on the surface;
   a sensor for detecting the total reflectivity of the test patch particles and the diffuse component of the total reflectivity of the test patch and generating a total signal indicative of the total reflectivity of the patch and a diffuse signal indicative of the diffuse component of the total reflectivity of the patch;
   a first circuit responsive to the difference between the total signal and the diffuse signal for generating a specular signal indicative of the specular component of the total reflectivity of the test patch;
   a second circuit for adding the total signal indicative of the total reflectivity of the test patch and the diffuse signal indicative of the diffuse component of the total reflectivity of the test patch and providing a sum signal; and
   a third circuit responsive to the difference of the sum signal and the specular signal to provide a total diffuse signal proportional to the diffuse component of the total reflectivity of the test patch.

6. An apparatus according to claim 5 including a first condenser lens interposed between said projecting means and the test patch to collimate light rays projected onto the marking particles on the surface.

7. An apparatus according to claim 6 including a second condenser lens for receiving the light rays reflected from the test patch.

8. An apparatus according to claim 7 wherein the sensor includes a photosensor array.

9. An apparatus according to claim 8 wherein said photosensor array includes:
   a central photosensor positioned to receive a signal proportional to the total light rays transmitted through said second condenser lens; and
   at least one edge photosensor positioned about the periphery of said central photosensor to receive a signal proportional the diffuse component of the light rays transmitted through said second condenser lens.

10. A densitometer, including:
    a collimating lens;
    a light source positioned to project light rays through said collimating lens;
    a collector lens positioned to receive reflected light rays;
    a photo sensor positioned to receive the reflected light rays transmitted through said collector lens and being adapted to generate signals proportional to the total light rays transmitted through said collector lens; and
    control circuitry electrically connected to said photosensor for responding to the signals proportional to the total light rays transmitted through said collector lens for generating a specular signal proportional to a specular component of the light rays transmitted through said collector lens, the control circuitry including a difference amplifier responding to the specular signal and the signals proportional to the total light rays to provide a diffuse signal proportional to the diffuse component of the total light rays transmitted through said collector lens,
    wherein the photo sensor is adapted to generate a total signal proportional to the total light rays transmitted through said collector lens and a diffuse signal proportional to the diffuse component of the light rays transmitted through said collector lens, and wherein the control circuitry includes a first circuit responsive to the difference between the total signal and the diffuse signal for generating the specular signal indicative of the specular component of the total reflectivity of a test patch including marking particles deposited on a photoconductive surface and a second circuit for adding the total signal and the diffuse signal providing a sum signal.

11. A densitometer according to claim 10 wherein the control circuitry includes a third circuit responsive to the difference of the sum signal and the specular signal to provide a total diffuse signal proportional to the diffuse component of the light rays transmitted through said collector lens.

12. A densitometer according to claim 10 wherein said photosensor includes:
    a central photosensor positioned to receive a signal proportional to the total light rays of the light rays transmitted through said collector lens; and
    at least one edge photosensor positioned about the periphery of said central photosensor to receive a signal proportional to the diffuse component of the total light rays of the light rays transmitted through said collector lens.

13. A densitometer according to claim 12, wherein said light source includes a light emitting diode.

14. A densitometer according to claim 10 further including means for measuring and controlling the intensity of the light rays being emitted from said light source.

15. A densitometer according to claim 14 wherein said measuring and controlling means includes a control photosensor positioned adjacent said light source to detect the variation in intensity of the light rays being emitted from said light source.

* * * * *